United States Patent [19]

Doyle, Jr. et al.

[11] Patent Number: 4,916,611
[45] Date of Patent: Apr. 10, 1990

[54] INSURANCE ADMINISTRATION SYSTEM WITH MEANS TO ALLOW AN EMPLOYER TO DIRECTLY COMMUNICATE EMPLOYEE STATUS DATA TO CENTRALIZED DATA STORAGE MEANS

[75] Inventors: Findley C. Doyle, Jr., Rochester; William D. Alcott, III, Grosse Pointe Farms, both of Mich.

[73] Assignee: Northern Group Services, Inc., St. Clair Shores, Mich.

[21] Appl. No.: 68,240

[22] Filed: Jun. 30, 1987

[51] Int. Cl.$^4$ .............................................. G06F 3/00
[52] U.S. Cl. .................................... 364/401; 364/403
[58] Field of Search ............ 364/401, 403, 413, 413.02

[56] References Cited

U.S. PATENT DOCUMENTS

| 4,491,725 | 1/1985 | Pritchard | 364/413 |
| 4,648,037 | 3/1987 | Valentino | 364/408 |
| 4,667,292 | 5/1987 | Mohlenbrock | 364/406 |
| 4,680,460 | 7/1987 | Drexler | 235/488 |

OTHER PUBLICATIONS

"Cobra Software Added to Flex Benefit Plans", National Underwriter: Life & Health/Financial Services Edition, V9, No. 9, p. 6, Mar. 1987.
"Bank Tames Cobra Administration", Business Insurance V21, N33, p. 16, Aug. 17, 1987, Donna DiBlase.
"Cobra Administration Software System", 08/87, Abstract from Microsearch File of Orbit.
Melnick, Irving, *The Urologic Clinics of North America*, Feb. 1986, pp. 53–54.
Leading Edge Nutshell Information Filer, Version 2.0 User's Manual, 1985, pp. 258–265.

*Primary Examiner*—Jerry Smith
*Assistant Examiner*—Gail O. Hayes
*Attorney, Agent, or Firm*—Krass & Young

[57] ABSTRACT

The computerized insurance claim processing system links the physician's office and the provider of insurance coverage by means of a central administration computer. The system provides up-to-date information to the provider of health care services as to insurance coverage of a patient. The system also allows real time modification of the information, including the identity of patients covered and the type of insurance benefits.

18 Claims, 7 Drawing Sheets

INSURANCE ADMINISTRATION SYSTEM WITH MEANS TO ALLOW AN EMPLOYER TO DIRECTLY COMMUNICATE EMPLOYEE STATUS DATA TO CENTRALIZED DATA STORAGE MEANS

The invention relates to computerized systems for processing insurance claims.

BACKGROUND OF THE INVENTION

A type of processing system for medical insurance claims is discussed in U.S. Pat. No. 4,491,725, issued to Pritchard, on January 1, 1985. This patent is incorporated by reference. The patent discusses a system in which a patient seeking medical treatment presents an identification card at a physician's office. Coded data is electronically read from the card, and transmitted to a central brokerage computer. The brokerage computer ascertains from a data base whether the patient is covered by an insurance policy, and, if so, whether the policy will fully pay for the medical treatment sought by the patient. The brokerage computer informs the physician immediately of the information found. The patent further discusses various types of funds transfer which can occur as payment for the medical treatment.

However, this patent does not appear to address the question of (1) How the information contained in the data base is derived, and (2) How and when the information in the data base is updated. The latter question can significantly affect the cost incurred by an employer in providing a group medical insurance plan for its employees. For example, the data base contains a roster of insured employees which must be updated as employees leave the employing company. However, because of various delays, some rosters are updated only once per month. This monthly updating has the result that an employee leaving the service of a company nevertheless retains the ability, whether intended or not, to obtain treatment under the medical insurance coverage until his name is removed from the roster. If a month is assumed to contain thirty days, then, on average, every employee who leaves the employment of a company retains insurance coverage for fifteen days afterward, at the employer's expense.

In addition, there is another possible source of expense to employers based on departing employees. The Consolidated Omnibus Budget Reconciliation Act of 1985 (COBRA) (P.L. 99-272) requires that, under certain circumstances, an employer must continue an employee's insurance coverage after terminating employment.

Both the occurrence of late roster updating, together with the existence of COBRA, create complications when a former employee seeks medical care, because they create uncertainty as to the insurance coverage of the employee. It is very important that the treating physician know whether the employee has insurance benefits.

OBJECT OF THE INVENTION

It is an object of the invention to provide an improved system for the administration of medical insurance claims.

SUMMARY OF THE INVENTION

In one form of the invention, a third party maintains a data base in an administration computer. The data base includes a comprehensive roster of all persons having insurance benefits under a given insurance plan, as well as the types of benefits available, including the particular medical treatments which are reimbursible by insurance, and the dollar value of the reimbursement for each treatment. A treating physician has communication equipment which can communicate in real time with the administration computer in order to ascertain whether a given patient is on the roster of covered individuals for a given insurance plan, and whether a proposed treatment is reimbursible, as well as the amount of reimbursement. If the data base indicates that the proposed treatment is in fact covered, the physician can request that the amount of reimbursement be immediately credited to him, as by a funds transfer to his bank.

An employer, who provides the insurance coverage for the benefit of an employee-patient, also has communication equipment which can link to the administration computer, but in a different manner than that of the physician: the employer can modify, in real time, the data base. For example, an employer can add and delete persons to the roster of those insured, as people enter and leave his employment. Further, the employer can change the benefits which the plan provides. For example, he may change the reimbursement amount for treatment of a sprained wrist from X dollars to Y dollars.

Further, the employer can audit the activity of his insurance plan as reported by the data base. For example, he can track, by addressing the data base, the insurance claim activity of each insured individual.

BRIEF DESCRIPTION OF THE DRAWINGS

FIGS. 2, 2a, 2b, 2c, 3, 3b, 3c, and 4-5 illustrate a flow chart which describes the operation of parts of the system of FIG. 1.

DETAILED DESCRIPTION OF THE INVENTION

Figure 1:
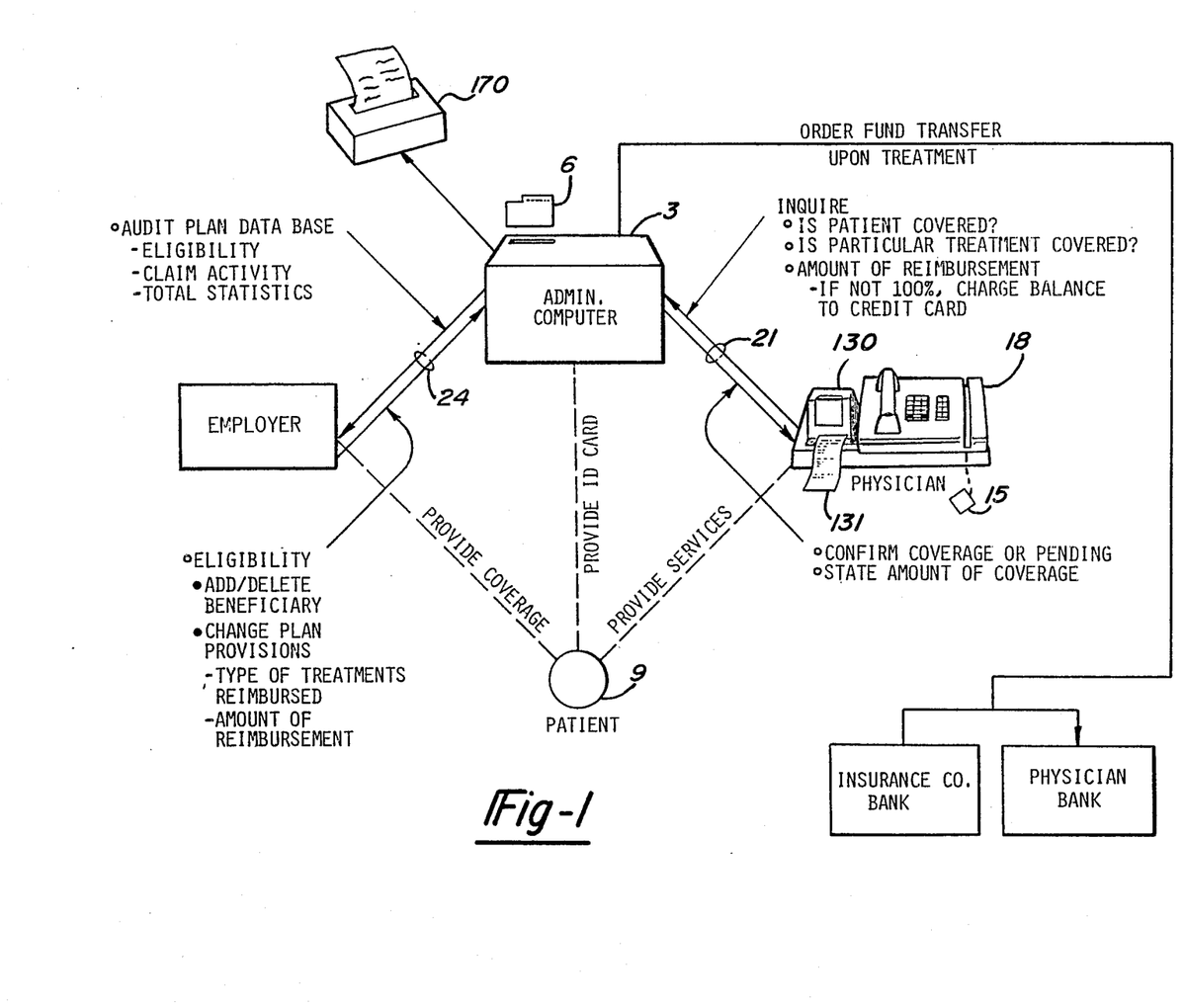
FIG. 1 illustrates a simplified overview of the system.

FIG. 1 depicts a simplified overview of one form of the invention. An administration computer 3 maintains a data base for each insurance plan provided by an employer. File 6 indicates the data base for plan ABC maintained by employer Alpha Company. The file includes a roster of all insured employees of Alpha Company, their spouses and dependents. In addition, the file includes a list of all medical treatments for which insurance compensation is available. (Each treatment is typically called a diagnosis, because the physician usually undertakes a diagnosis prior to embarking upon the treatment which the diagnosis indicates. An example would be a diagnosis of a sprained wrist in a patient Adam, followed by the treatment considered proper under the circumstances.) The file also contains a list of dollar amounts payable for each type of diagnosis. For example, in the file, X dollars is associated with the diagnosis for sprained wrist, meaning that insurance plan ABC will pay X dollars for the treatment of a sprained wrist.

When a patient 9 visits a physician for treatment of the sprained wrist, the patient 9 presents an identification card 15 as evidence that the patient is covered by insurance plan ABC. The physician, using data terminal 18, communicates with the administration computer 3 on data link 21, and states to the computer the identity of the patient (Adam), the name of the patient's plan (ABC in this case) together with the diagnosis (sprained wrist). A computer 3 locates the file corresponding to plan ABC, confirms that the patient Adam is on the roster of insured persons, confirms whether the plan ABC will pay the physician for the given diagnosis (sprained wrist) and states the amount of reimbursement. In response, the physician can request the computer 3 to arrange a transfer of funds as payment.

If the amount of reimbursement is less than the normal charge made by the physician, a balance would exist. The physician then gives the patient an option of charging the balance to the patient's credit card. If the patient wishes to do so, the patient provides a suitable credit card number, which is communicated to the computer 3, which appropriately charges the patient's credit card account.

In addition, the computer stores the diagnosis and the amount paid to the physician, together with other relevant data, in a separate file associated with the patient's name. Thus, the file for plan ABC is updated at the time of treatment, and, further, the physician's office itself does the updating, although in an indirect manner.

The employer which provides insurance coverage to patient 9 also has access to the administration computer 3 along data link 24. However, the employer has access to a wider range of data in the file for the ABC plan than does the physician. As stated above, the physician only has access to data indicating whether or not a particular diagnosis is covered, the amount of reimbursement, and other similar data. In contrast, the employer has access to all data contained within the file for the ABC plan. Further, the employer can modify the data in the file. For example, the employer can add and delete the names of insured persons as appropriate. Still further, the employer can change the benefits provided by the plan ABC as needed. For example, the employer can change the types of diagnoses for which reimbursement will be allowed. The employer may decide that elective cosmetic facial surgery as distinct from restorative facial surgery used to restore damage caused by an accident, should not be a cost borne by plan ABC, but should be paid by the patient. In such a case, the employer would change the file to so indicate.

The employer can also change the dollar amount of reimbursement for a given diagnosis. For example, the employer may change the dollars reimbursements for a sprained wrist from X dollars to Y dollars.

In addition, the employer Alpha can audit the operation of his own plan ABC. For example, the roster of insured persons is available to him, so that he knows information as to the eligibility of his employees for insurance benefits. Also, as mentioned above, the computer 3 stores the diagnosis and treatment information as they occur. This allows the employer to retrieve such information and to evaluate the insurance claim activity of his employees. The employer can also make detailed statistical analyses of claim activity and plan expenditures by using the data available. FIGS. 2-5 contain a flow chart describing in more detail the operation of the system of FIG. 1 and will now be considered.

Figures 2, 2A:
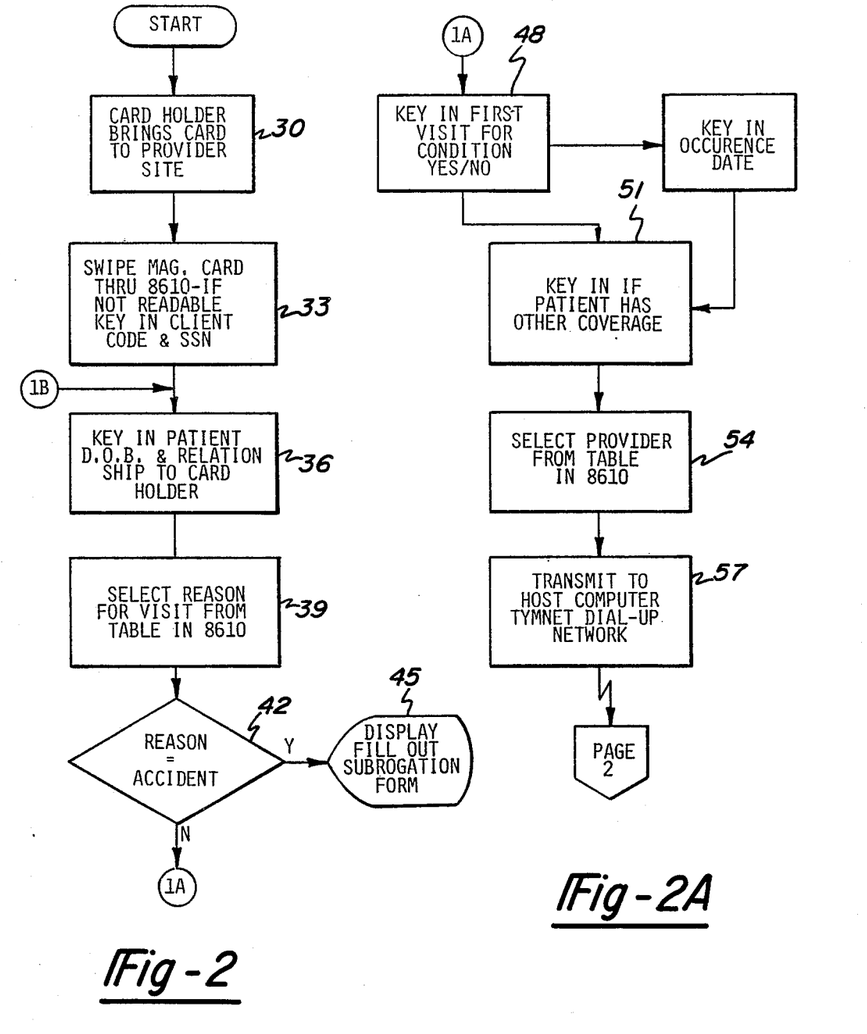

Block 30 in FIG. 2 indicates that a card holder (i.e., a patient) brings his card (the card 15 in FIG. 1) to a provider site. "Provider site" is a term in the art used to refer to one who provides medical services, namely, a physician or hospital. Block 33 indicates that the card is read by an "8610". "8610" is shorthand notation for a Datatrol 8610 computer terminal and associated printer indicated by numeral 18 in FIG. 1. This equipment is available from Datatrol Corporation, located in Minnetonka, Minnesota. Block 33 indicates that if the card is not readable, then an operator at the provider site types in the client's identification symbol, namely, his social security number (SSN), and a client code, which is a number identifying the ABC plan, from which insurance coverage is sought.

Block 36 indicates that the patient's date of birth (DOB) and relationship to the card holder is keyed into the terminal. In this example, the relationship is "employee", because Adam himself is seeking treatment. Were his wife to do so, the relationship would be "spouse".

Blocks 33 and 36 provide identification of the patient in order to assure that only the actual patient whose name is on the plan's roster receives medical treatment, and that no imposters do.

Block 39 refers to statement of a reason for the visit to the physician selected from a table. One type of table includes four reasons, namely, the reasons of illness, prevention, maternity or accident. The reason for the visit can be important for insurance purposes because different insurance coverage may be available for different reasons motivating a visit. For example, plan ABC may provide maternity benefits for Adam's wife, but not his daughter. Further, some reasons, such as accident, can cause legal rights to arise for the benefit of in the plan, and so special procedures should be taken. For example, the YES (Y) path leading from block 42 indicates that an accident motivated the visit to the physician's office. Block 45 indicates that the computer terminal prompts the patient to complete a subrogation form which can give certain subrogation rights to the plan ABC. For example, an automobile accident may have caused the condition, so that an automobile insurance company may have a liability to the patient or to Plan ABC.

Block 48 indicates that the patient states whether he has previously been treated for the present condition. As block 51 indicates, another insurance plan may be liable to the patient for the condition. For example, a wife may be employed and have insurance benefits making the husband's plan primarily liable, meaning that the patient and the wife's plan are only liable after the husband's plan pays. Block 54 indicates that the identity of the provider is selected (i.e., the physician) from a table of codes.

The inventors point out that, up to block 54 in FIG. 2A, no communication with the administration computer has yet been undertaken. However, at block 57, the local terminal 18 in the physician's office communicates data via a local telephone call to the administration (i.e., host) computer 3. Blocks 63, 66 and 68 indicate that block 71 is reached if the data base for plan ABC indicates that (1) the proper social security number, (2) proper provider, (3) proper date of birth and (4) proper relationship have been given by the patient. If not, circles 3A and 3B are reached, as will be later discussed.

Figures 2B, 2C:
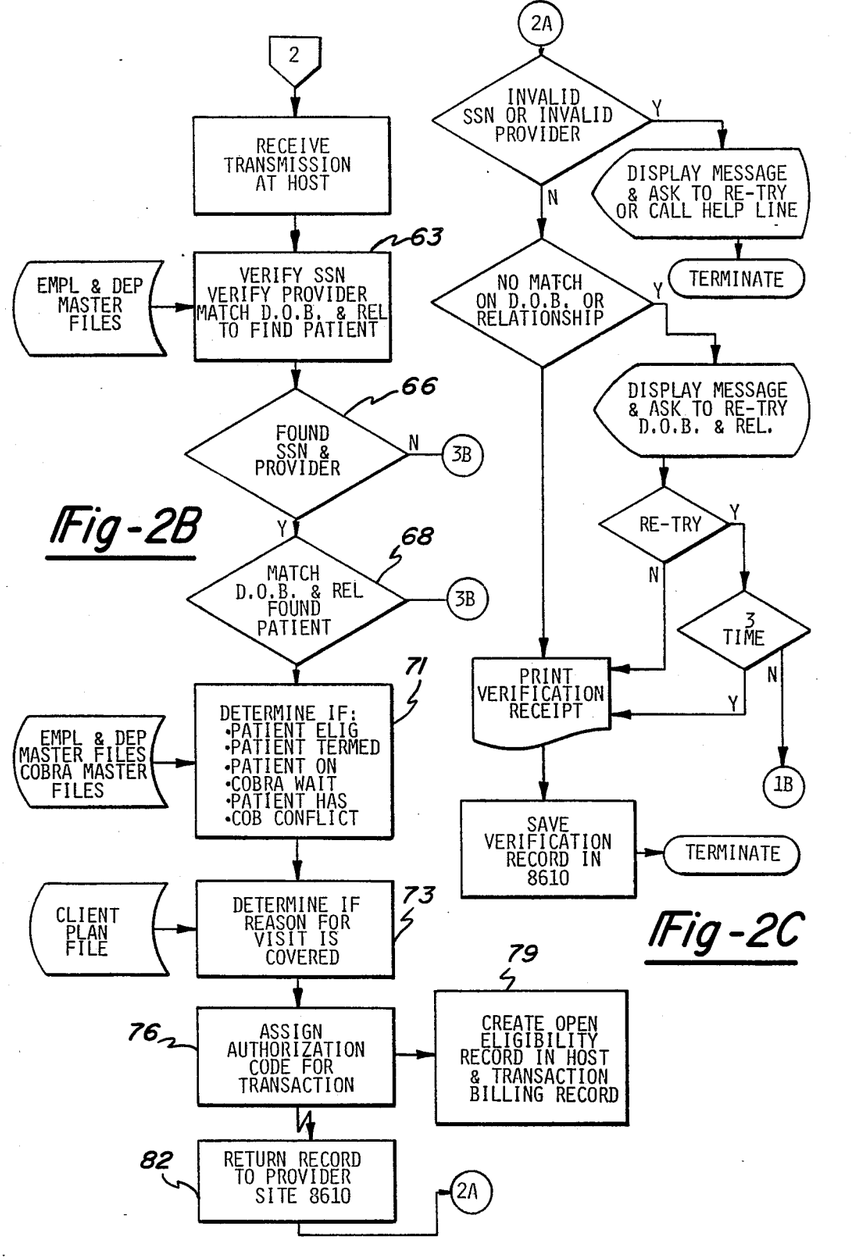

Restated, reaching block 71 indicates that the patient is not an imposter. Now it must be ascertained whether the person has insurance coverage. Block 71 indicates that the administration computer searches the roster to determine this. If the patient is found on the roster, then block 73 is reached. (The other situations indicated in block 71 will be discussed later.) Block 73 refers to a search by the administration computer of the data base of plan ABC to ascertain whether the reason for the visit in block 39 in FIG. 2 is covered (i.e., reimbursible)

by plan ABC. In addition, thought not indicated in FIG. 2B, block 73 can determine at this time whether the diagnosis (i.e., sprained wrist) is covered.

If the visit is covered, block 76 refers to the assignment of an authorization code for the transaction (i.e., treatment). An authorization code is a unique symbol, which identifies the transaction in an unmistakable manner as eligible for treatment. The authorization code functions to facilitate bookkeeping, much in the way that a serial number on an invoice for other purchases does so.

Block 79 refers to the creation of an eligibility record in the administration computer. This refers to an allocation of memory space, having the authorization code as an address, in anticipation of data which will later be received from the physician, after treatment has been completed. Block 82 indicates that the eligibility record is transmitted to the physician's terminal. This means that an indication that the patient is in fact on the plan's roster, together with an affirmation that the reason for the visit is covered, is transmitted. One type of message indicating eligibility would be "eligibility approved". In addition, the authorization code assigned in block 76 is transmitted. The blocks in FIG. 2C following block 82 relate to error handling and are considered self-explanatory. The block labeled "terminate" indicates that the telephone connection is terminated.

At this time a physician has information indicating that treatment of the diagnosed condition is covered by insurance. Following treatment, the physician, as indicated by block 85 in FIG. 3, enters authorization code into his local terminal in FIG. 1. Blocks 88 and 91 indicate that the local terminal searches and finds the patient's name, Adam, so that the treatment portion of the transaction can be completed and transmitted to the administration computer.

Figures 3, 3A:
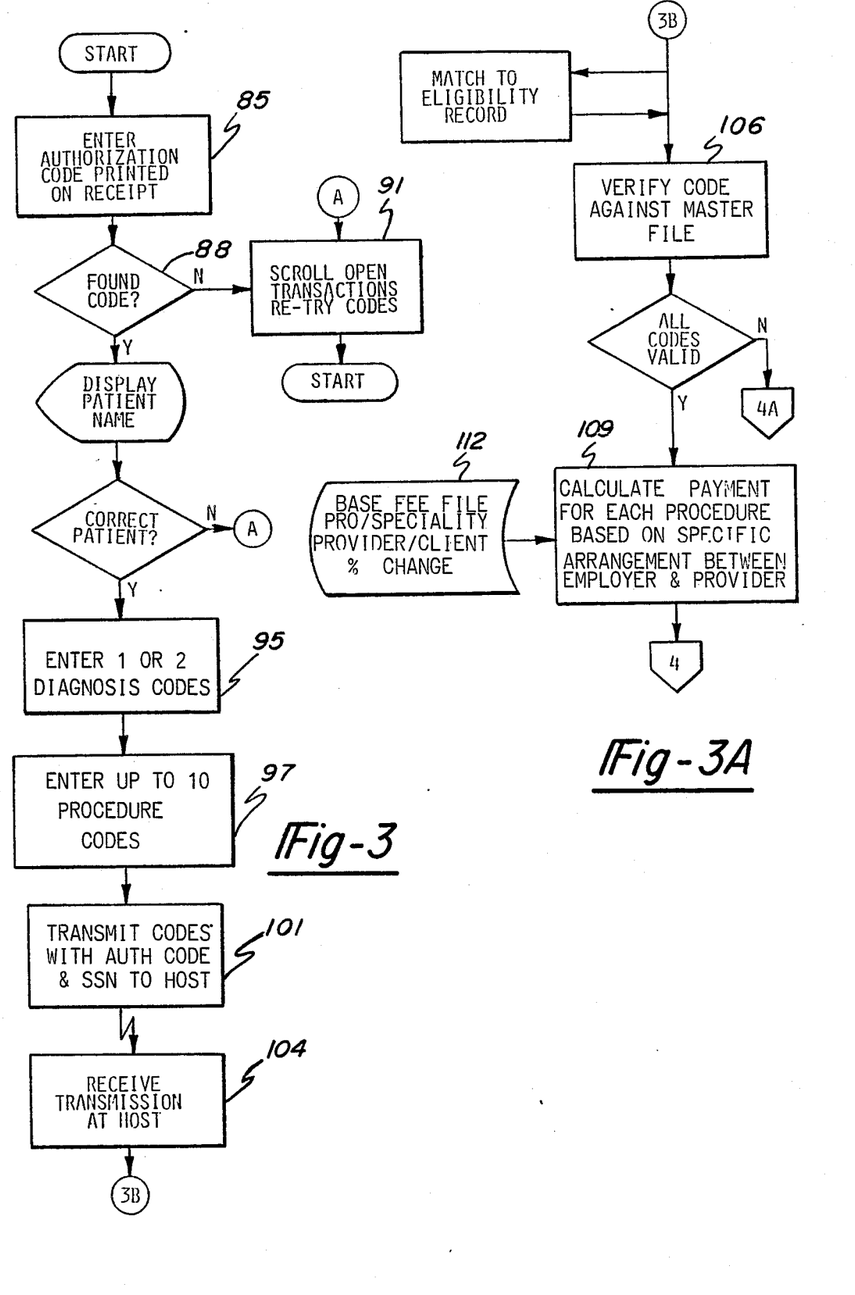

Block 95 indicates that the physician enters a code identifying the diagnosis (sprained wrist). Block 97 indicates that the physician enters up to ten "procedure codes", which refer to the treatments for a sprained wrist selected by the physician. Blocks 101 and 104 indicate that the diagnosis and procedure codes are now transmitted via a local telephone call to the administration computer 3. Block 106 indicates that a check is made to verify that the codes received are actually existing, and not fictitious, codes. Block 109 indicates that the administration computer searches the data base for plan ABC and calculates the reimbursement specified by the employer for each treatment. Block 112 indicates that these reimbursements are under the employer's control, and will be discussed later in more detail. Block 115 ascertains whether the present diagnosis (sprained wrist) is covered by plan ABC, whether the given treatments (e.g., anaesthetics applied, immobilization by a plaster cast) are covered, the dollar amounts of the coverage, and whether a deductible amount or a co-payment apply. As indicated by blocks 118 and 121, data regarding the net payment which the plan ABC will reimburse the physician is transmitted to the physician's terminal. A printer 130 prints the relevant data on a receipt 131, as indicated by block 125. The patient signs the receipt as ackowledgement that treatment was done. Block 135 indicates that the data link between the physician's terminal and the administration computer is then terminated.

Figure 4:
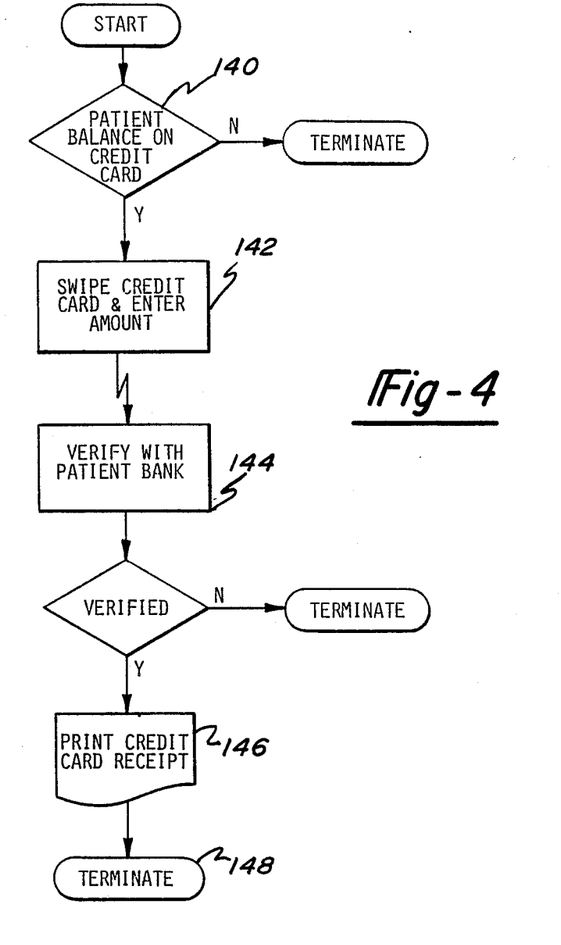

At this point, the patient's identity has been verified, as well as his coverage under plan ABC (i.e., his elibility). Also, the diagnosis and treatments have been transmitted to the administration computer, wherein they are stored for future use, and the administration computer has transmitted to the physician's terminal the reimbursement amounts for the treatments involved. It is possible that the reimbursement amounts are less than the physician's customary charges for the treatments that the patient owes a deductible, or that the computer 3 found the patient or the treatments to be non-insured, with the result that a balance of payment remains. FIG. 4 describes an option under which the patient can charge the balance to a credit card. The YES path from block 140 indicates that the charges are to be placed upon a credit card account. Block 142 indicates that the necessary information is either electronically read ("swiped"), or directly typed into the physician's terminal, together with the dollar amount. At this time, the data link is established between the physician's terminal and the administration computer. Block 144 indicates that the administration computer verifies with the bank issuing the credit card has stated that the balance amount can be properly applied to the credit card account. If so, block 146 is reached, wherein the necessary information is printed by printer 130 in FIG. 1 upon a receipt 131, and the data link is terminated by block 148.

Figure 5:
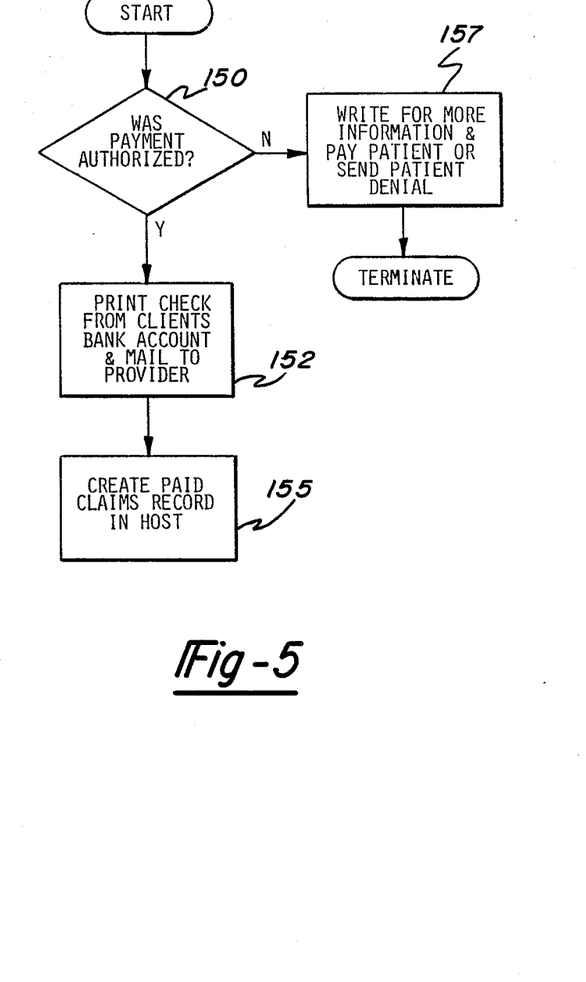

FIG. 5 indicates one procedure for providing plan payment to the physician. The inquiry of block 150 refers to the authorization discussed in connection with block 76 in FIG. 2B, wherein the authorization code was established and stored. If payment was authorized, block 152 is reached, which indicates that a check is drawn on the client's bank account and mailed to the provider. This means that the administration computer prints a bank check drawing upon a bank account which is funded by plan ABC, or by the insurance company itself, and mailed to the provider, that is, to the physician. Block 155 indicates that the administration computer maintains a record of checks printed in block 152. The record is available to the employer and the insurance company through data link 24 in FIG. 1. Further discussion of systems which accomplish the funds transfer described in FIGS. 4 and 5 is found in U.S. Pat. No. 4,346,442, Musmanno, 1982, which is incorporated by reference.

If block 150 indicates that no payment was authorized, then block 157 indicates that a message, indicating that payment is not authorized, is sent to the physician's terminal.

The preceding discussion has been chiefly concerned with aspects of verification. That is, verification of the patient's identity was undertaken, verification that the diagnoses and treatments were of the type which a given plan (ABC) would reimburse, and verification or ascertainment of the dollar amounts reimbursible for each treatment. However, in some circumstances, a system of notification and tracking of former employees may be desirable, as discussed above, in order to comply with contractual or statuatory requirements. One such system will now be described in connection with the following Table 1. Table 1 outlines a sequence of steps taken by, and in connection with, the administration computer.

TABLE 1

1. Delete Adams, spouse, and dependents from roster of insured persons.
2. Notify Adams and perhaps others of the termination of insurance coverage. Notify them that they have the option within X days to continue certain insurance benefits at stated premium rates. Send these notices by certified mail.
3. If notified persons respond within predetermined time, indicating desire to purchase insurance, print and send a package of payment coupons for making periodic payments.
4. If participants make no response within the predetermined time, record this fact in the data base for plan ABC.
5. (Optional) If, as in paragraph 4, no response has been received, print and transmit to the former participants a second, backup notice.

Line 1 in Table 1 indicates that the Adams family is deleted from the roster of insured persons under the ABC plan, perhaps because of termination of employment. This is done directly by the employer or data link 24. One significant consequence of this deletion from the roster is that, should a physician make inquiry using the physician's data link 21, the administration computer has information, almost on an immediate basis, allowing the computer to inform the physician that the Adams family is no longer covered by the ABC plan. However, in some cases, discussed later, the computer may refrain from stating that the family is not covered by the ABC plan, and instead indicate that the family presently has an indeterminate status as to coverage.

Upon deletion of the Adams' participants from the plan, and if the employer so requests, either at the time of deletion, or at a prior time, administration computer 3 activates a printer 170 which prints a notice which is transmitted to one or more members of the family, notifying them of the fact of termination, and offering them the option to purchase within a stated period of time the same or similar insurance which they previously had, at stated premium rates. The letter is transmitted to the Adams family, and the administration computer then sets into motion a programming routine, known in the art, to track the response of the Adams's family, when it occurs.

If one or more of the family members respond favorably, in writing, an operator enters the proper data into the administration computer. In response, the computer, using printer 170, prints a group of payment coupons, which are mailed to the electing participants. The participants return the coupons with payment, on a periodic basis, and the coupons assist the administration computer in tracking the payment history of the electing participants. The coupons bear sufficient information to do this, and can be machine-readable by the administration computer, as known in the art.

If no response is received in the stated time, the computer, having an internal time clock, as known in the art, notifies the data base for plan ABC, and programming steps are taken to change the status of the Adams family from indeterminate to terminated, as will now be discussed.

As was stated earlier, it may be the case that an option was given to the Adams family to elect to purchase insurance within a stated time period. This option can be given in fulfillment of a collective bargaining agreement, state or federal statutes, as discussed earlier, or for other reasons. Further, the option may have certain retroactive aspects. For example, the employer may be required to give the former employee the right to exercise the option for a stated period of time, such as sixty days. If the option is retroactive, the following sequence of events can occur. Termination of employment can occur on July 1. The notice described in Line 2 of Table 1 can be sent on the same day, July 1. The notice can be received by the employee on July 2 and the notice can give him sixty days within which to decide whether to purchase insurance. The employee may visit a physician on July 15, but before he exercised the option. If he exercises the option on July 20, and pays the insurance premium as required, the ABC plan may be required to pay for the July 15 visit to the physician. Therefore, the administration computer, in searching the data base in response to the physician's inquiry on July 15, classifies the Adams family as indetermines until the option is exercised, or the option expires.

Continuing the example, if the option expires on September 1, without being exercised, and if Adams visits a physician on September 10, the administration computer, in response to the physician's inquiry states that Adams is terminated from the ABC plan, and not under indeterminate status. Further, the classification was made by the computer immediately upon expiration of the option, which was a stated period, (sixty days in this case) after mailing of the notice discussed in Line 2 of Table 1.

Several important aspects of the invention are the following:

1. As FIG. 1 indicates, an employer can add and delete beneficiaries, as well as change provisions of a plan, by using data link 24. Further, as the discussion above indicates, these changes can be done in real time, causing the currency of the data base to be limited only by the diligence of the employer. The fact that the data base is current has two significant results: first, the average lag period of fifteen days, discussed above, is eliminated. Therefore, a former employee cannot exploit the existence of the lag and obtain treatment, because treating physicians will be able to know immediately when an employee is deleted from the roster of insured persons.

A second result relates to COBRA requirements. The occurrence of updates to the roster can trigger the notification procedure described above into action. For example, detection routine, or circuit, known in the art, detects a deletion of a person from the roster and, in response, immediately causes a notification to be sent, as outlined in Table 1. The immediate notification prevents COBRA mandated insurance from arising at the employer's expense.

These two results are similar in the respect that they both limit the liability, borne by an employer, which arises through the running of time. Viewed another way, the same event which eliminates the fifteen-day lag in insurance termination (i.e., the event of real-time deletion from the roster) also triggers into action the notification procedure of Table 1.

2. The computation of the patient's bill, discussed in connection with block 118 in FIG. 3B, includes a computation of any deductible amount owed by the patient. This is possible because the administration computer retains records of all insurance activity by the patient Adam. For example, if Adams has a One Hundred Dollar deductible amount per year, if Adam has received no other treatment in the year, and if the charge for the present treatment is Eighty Dollars, the entire Eighty Dollars is paid by Adam. This fact is indicated on the bill printed by terminal 18 in FIG. 1.

Figure 3B:
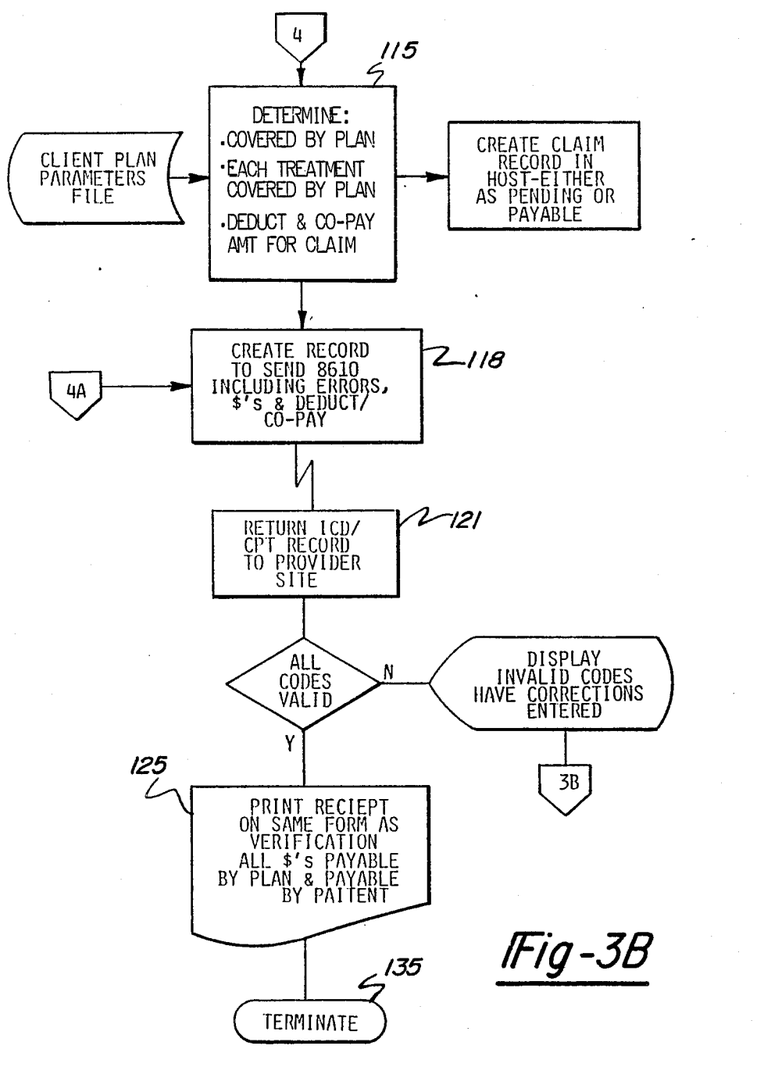

Block 118 also indicates the administration computer calculates any co-payment amounts. This refers to amounts which the patient may be required to co-pay with the plan ABC. For example, Plan ABC may pay fully for treatments for sprained wrists, but only pay one-half for cosmetic facial surgery. In the latter case, the patient co-pays the remaining one-half.

3. The preceding discussion has been made in the context of a patient visiting a physician. However, it should be understood that the invention can be used by any provider of health care services, including physicians, dentists, hospitals, pharmacists, podiatrists, chiropodists, and psychologists. In this respect, a programming routine can be added which examines whether the given provider is authorized to perform the treatment for which payment is sought. For example, a podiatrist may not be authorized by state law to perform some types of surgery. The limits on the treatments which a provider can perform are stored in the administration computer, and are retrieved at the time the identity of the provider is verified, in block 63 in FIG. 2B. The routine prevents payments to unauthorized providers.

4. The card 15 in FIG. 1, which is carried by the patient, is the only card used by him, irrespective of the type of health benefits sought. That is, the patient presents the same card to his dentist, his pharmacist, his psychologist, etc.

5. A telephone connection between the physician's terminal 18 and the administration computer, and also between the administration computer and the employer, has been discussed. The preferred telephone connection uses a communications network, known in the art, such as Tymnet, available from McDonnel Douglas Corporation. The network allows a physician in one city to communicate with the administration computer located in a different city, by making a local, non-toll, telephone call.

6. If the patient has recently terminated employment, and then seeks medical treatment, the administration computer, as outlined in Table 1, records the patient's insurance status as indeterminate and informs the physician accordingly. In such a case, the physician must decide the manner in which to collect payment, as plan ABC makes no commitment at this time.

7. The invention has been described in terms of health benefits claims. However, it is applicable to any generic plan under which a third party pays money for the benefit of a beneficiary. One example is a food stamp program, in which a beneficiary presents food stamps (i.e., the "card" 15 in FIG. 1) to a supermarket (the "provider") which can verify, using terminal 18, whether the stamps are valid, and whether the beneficiary is entitled to use them. In this case, the roster is a roster of food stamp beneficiaries.

In another example, a governmental workman's compensation program is treated as analogous to plan ABC, and provides payment.

8. In addition to the verification procedures described above for verifying the identity of the patient, other procedures can be used. Voiceprint, fingerprint, and signature verification can be used, as known in the art.

9. From one point of view, the invention allows the physician to only address and read the data base, while the employer can address, read, and, in addition, modify the data base, as by deleting beneficiaries. (Of course, the physician, in a sense, can modify the data base, because the treatments which he performs are stored by the administration computer. However, this type of modification does not affect the benefits available to beneficiaries. The employer can modify the benefits.

10. FIG. 4 describes an optional procedure by which a patient can pay the balance which plan ABC does not cover. FIG. 5 describes a procedure by which plan ABC pays the physician.

11. Plan ABC has been described as an insurance plan. However, it need not be such. Plan ABC can be a self-insurance plan of the employer, or any entity which provides benefits to beneficiaries for specified types of health care.

An invention has been described wherein a physician, at the time and location of rendering medical treatment, obtains information as to the amount of payment for the treatment, and also, in some cases, actual payment itself. The information is obtained from a database which is updated, in real time, by the employer providing the insurance.

Numerous substitutions and modifications can be undertaken without departing from the true spirit and scope of the invention as defined in the claims. What is desired to be covered by Letters Patent is the invention as defined in the following claims.

What is claimed is:

1. In a health care benefits administration system of the type having a computer system for storing and processing information in a database containing records of patients and medical benefits, the improvement comprising:

said database having an eligibility file of a plurality of patients for which medical benefits are provided by a given benefits sponsor;

said eligibility file including a benefits status record for storing one of a plurality of states, including at least an active state and a pending state, for each patient;

a benefits sponsor terminal communicating on line with said computer system and directly accessible by said benefits sponsor for input of data indicating that benefits provided by said sponsor for a particular patient should be added or terminated;

said computer system being preprogrammed to automatically alter said status record for said given patient to said active state when said data input by said benefits sponsor indicates that benefits are to be added for said patient;

said computer system being preprogrammed to automatically alter said status record for said given patient to said pending state when said data input by said benefits sponsor indicates that benefits are to be terminated for said patient;

notification generating means controlled by said computer system for automatically providing notice to a patient of a change in said status record from an active state to a pending state.

2. The administration system of claim 1 wherein the administration system is accessible to service providers which provide medical services to patients, the improvement further comprising:

at least one service provider terminal communicating on line with said computer system and directly accessible by said service provider for input of data indicating the identity of a patient and for receiving from said computer system an indication of the eligibility of said patient for medical benefits;

said computer system being preprogrammed to interrogate said status record in response to input of data from said service provider terminal and to supply an indication at said service provider terminal of whether said status record for said patient is at said pending state.

3. The benefits system of claim 1 wherein said status record is capable of storing a special active state in addition to said active state and said pending state, said special active state indicating that a given patient has been terminated by the benefits sponsor and said patient has elected to continue to receive medical benefits.

4. The administration system of claim 3 wherein said status record is further capable of storing a terminated state in addition to said active state, said special active state and said pending state;
  wherein said computer system includes time clock means for ascertaining elapsed time; and
  wherein said computer system is preprogrammed to interrogate said status record and to automatically change a pending state to a terminated state in response to a predetermined elapsed time.

5. The administration system of claim 1 wherein said status record is capable of storing a terminated state in addition to said active state and said pending state;
  wherein said computer system includes time clock means for ascertaining elapsed time; and
  wherein said computer system is preprogrammed to interrogate said status record and to automatically change a pending state to a terminated state in response to a predetermined elapsed time.

6. The administration system of claim 1 wherein said computer system includes time clock means for ascertaining elapsed time; and
  wherein said computer system is preprogrammed to interrogate said status record and to automatically remove a patient from said eligibility file when said status record for that patient has been in the pending state for a predetermined elapsed time.

7. In a medical benefits administration system of the type having a computer system for storing and processing information in a database containing records of patients and medical benefits, and having a plurality of service provider terminals attached to said computer system for use by service providers in interacting with said computer system, the improvement comprising:
  said database having a patient file identifying each of said plurality of medical benefits plans under which each patient has coverage;
  said database having an eligibility file of a plurality of patients for which medical benefits are provided by a given benefits sponsor;
  said eligibility file including a benefits status record for storing one of a plurality of states, including at least an active state and a pending state, for each patient;
  a benefits sponsor terminal communicating on line with said computer system and directly accessible by said benefits sponsor for input of data indicating that benefits provided by said sponsor for a particular patient should be added or terminated;
  said computer system being preprogrammed to automatically alter said status record for said given patient to said active state when said data input by said benefits sponsor indicates that benefits are to be added for said patient;
  said computer system being preprogrammed to automatically alter said status record for said given patient to said pending state when said data input by said benefits sponsor indicates that benefits are to be terminated for said patient;
  notification generating means controlled by said computer system for automatically providing notice to a patient of a change in said status record from an active state to a pending state;
  said computer system being preprogrammed to receive from said service provider terminal identity data indicative of the identity of a given patient and service data indicative of the services for which payment is requested;
  said computer system being preprogrammed to access said patient file in response to said identity data and to ascertain the medical benefits plans under which said patient has coverage.

8. The administration system of claim 7 wherein said patient file includes a record capable of identifying one of a plurality of medical benefits plans as a primary plan and at least one other of said plurality of medical benefits plans as a secondary plan; and
  wherein said computer system is preprogrammed to coordinate benefits for a given patient between said primary and secondary plans.

9. The administration system of claim 7 wherein said service provider terminal communicates on line with said computer system and receives from said computer system an indication of the eligibility of said patient for medical benefits.

10. The administration system of claim 7 wherein said service provider terminal communicates on line with said computer system and receives from said computer system an indication of the amounts payable under such medical benefits plans for the services indicated by said service data.

11. In a medical benefits administration system of the type having a computer system for storing and processing information in a database containing records of patients and medical benefits, and having a plurality of service provider terminals attached to said computer system for use by service providers in interacting with said computer system, the improvement comprising:
  said database having a plan parameters file having a record of coverage parameters including amounts paid for specified treatments under a plurality of medical benefits plans;
  said database having a patient file identifying each of said plurality of medical benefits plans under which each patient has coverage;
  said database having an eligibility file of a plurality of patients for which medical benefits are provided by a given benefits sponsor;
  said eligibility file including a benefits status record for storing one of a plurality of states, including at least an active state and a pending state, for each patient;
  a benefits sponsor terminal communicating on line with said computer system and directly accessible by said benefits sponsor for input of data indicating that benefits provided by said sponsor for a particular patient should be added or terminated;
  said computer system being preprogrammed to automatically alter said status record for said given patient to said active state when said data input by said benefits sponsor indicates that benefits are to be added for said patient;
  said computer system being preprogrammed to automatically alter said status record for said given patient to said pending state when said data input by said benefits sponsor indicates that benefits are to be terminated for said patient;

notification generating means controlled by said computer system for automatically providing notice to a patient of a change in said status record from an active state to a pending state;

said computer system being preprogrammed to receive from said service provider terminal identity data indicative of the identity of a given patient and service data indicative of the services for which payment is requested;

said computer system being preprogrammed to access said patient file in response to said identity data and to ascertain the medical benefits plans under which said patient has coverage;

said computer system being preprogrammed to access said plan parameters file for each of the medical benefits plans so ascertained to determine the amounts payable under such medical benefits plans for the services indicated by said service data.

12. The administration system of claim 11 wherein said patient file includes a record capable of identifying one of a plurality of medical benefits plans as a primary plan and at least one other of said plurality of medical benefits plans as a secondary plan; and wherein said computer system is preprogrammed to coordinate benefits for a given patient between said primary and secondary plans.

13. The administration system of claim 11 wherein said service provider terminal communicates on line with said computer system and receives from said computer system an indication of the eligibility of said patient for medical benefits.

14. The administration system of claim 11 wherein said service provider terminal communicates on line with said computer system and receives from said computer system an indication of the amounts payable under such medical benefits plans for the services indicated by said service data.

15. In a medical benefits administration system of the type having a computer system for storing and processing information in a database containing records of patients and medical benefits, and having a plurality of service provider terminals attached to said computer system for use by service providers in interacting with said computer system, the improvement comprising:

said database having a plan parameters file having a record of coverage parameters including amounts paid for specified treatments under a plurality of medical benefits plans;

said database having an eligibility file of a plurality of patients for which medical benefits are provided by a given benefits sponsor;

said eligibility file including a benefits status record for providing one of a plurality of states, including at least an active state and a pending state, for each patient;

a benefits sponsor terminal communicating on line with said computer system and directly accessible by said benefits sponsor for input of data indicating that benefits provided by said sponsor for a particular patient should be added or terminated;

said computer system being preprogrammed to automatically alter said status record for said given patient to said active state when said data input by said benefits sponsor indicates that benefits are to be added for said patient;

said computer system being preprogrammed to automatically alter said status record for said given patient to said pending state when said data input by said benefits sponsor indicates that benefits are to be terminated for said patient;

notification generating means controlled by said computer system for automatically providing notice to a patient of a change in said status record from an active state to a pending state;

said computer system being preprogrammed to receive from said service provider terminal identity data indicative of the identity of a given patient and service data indicative of the services for which payment is requested;

said computer system being preprogrammed to access said plan parameters file for each of the medical benefits plans so ascertained to determine the amounts payable under such medical benefits plans for the services indicated by said service data.

16. The administration system of claim 15 wherein said service provider terminal communicates on line with said computer system and receives from said computer system an indication of the eligibility of said patient for medical benefits.

17. The administration system of claim 15 wherein said service provider terminal communicates on line with said computer system and receives from said computer system an indication of the amounts payable under such medical benefits plans for the services indicated by said service data.

18. In a medical benefits administration system of the type having a computer system for storing and processing information in a database containing records of patients and medical benefits, and having a plurality of service provider terminals attached to said computer system for use by service providers in interacting with said computer system, the improvement comprising:

said database having a plan parameters file having a record of coverage parameters including amounts paid for specified treatments under a plurality of medical benefits plans;

said database having a patient file identifying each of said plurality of medical benefits plans under which each patient has coverage;

said database having means for establishing a hierarchy among each of said plurality of medical benefits plans for a given patient, identifying at least a primary plan and a secondary plan;

said database having an eligibility file of a plurality of patients for which medical benefits are provided by a given benefits sponsor;

said eligibility file including a benefits status record for storing one of a plurality of states, including at least an active state and a pending state, for each patient;

a benefits sponsor terminal communicating on line with said computer system and directly accessible by said benefits sponsor for input of data indicating that benefits provided by said sponsor for a particular patient should be added or terminated;

said computer system being preprogrammed to automatically alter said status record for said given patient to said active state when said data input by said benefits sponsor indicates that benefits are to be added for said patient;

said computer system being preprogrammed to automatically alter said status record for said given patient to said pending state when said data input by said benefits sponsor indicates that benefits are to be terminated for said patient;

notification generating means controlled by said computer system for automatically providing notice to a patient of a change in said status record from an active state to a pending state;

said computer system being preprogrammed to receive from said service provider terminal identity data indicative of the identity of a given patient and service data indicative of the services for which payment is requested;

said computer system being preprogrammed to access said patient file in response to said identity data and to ascertain the medical benefits plans under which said patient has coverage;

said computer system being preprogrammed to access said plan parameters file for each of the medical benefits plans so ascertained to determine the amounts payable under such medical benefits plans for the services indicated by said service data;

said computer system being preprogrammed to access said hierarchy establishing means in so determining the amounts payable, whereby said secondary plan is applied to amounts not payable under said primary plan to thereby maximize the total amounts payable on behalf of said patient without cumulative ovepayment by said primary and secondary plans.

* * * * *

UNITED STATES PATENT AND TRADEMARK OFFICE
CERTIFICATE OF CORRECTION

PATENT NO. : 1,916,611

DATED : April 10, 1990

INVENTOR(S) : Findley C. Doyle, Jr./William D. Alcott, III

It is certified that error appears in the above-identified patent and that said Letters Patent is hereby corrected as shown below:

Column 2, line 35, "3b, 3c" should be --3a, 3b--.

Column 8, line 12, "indetermines" should be --indeterminate--.

Column 13, line 53, "providing" should be --storing--.

Signed and Sealed this

Thirtieth Day of October, 1990

Attest:

HARRY F. MANBECK, JR.

Attesting Officer

Commissioner of Patents and Trademarks

UNITED STATES PATENT AND TRADEMARK OFFICE
CERTIFICATE OF CORRECTION

PATENT NO. : 4,916,611

DATED : April 10, 1990

INVENTOR(S) : Findley C. Doyle, et al

It is certified that error appears in the above-identified patent and that said Letters Patent is hereby corrected as shown below:

Column 5, line 1, "thought" should be --though--

Column 9, line 68, after "benefits" insert --)--

Column 16, line 12 "ovepayment" should be --overpayment--

Signed and Sealed this

Ninth Day of April, 1991

*Attest:*

HARRY F. MANBECK, JR.

*Attesting Officer*

*Commissioner of Patents and Trademarks*